United States Patent [19]

Watanabe

[11] Patent Number: 5,031,632
[45] Date of Patent: Jul. 16, 1991

[54] METHOD FOR THE INSTRUMENTATION OF SIZES OF RETINAL VESSELS IN THE FUNDUS AND APPARATUS THEREFOR

[76] Inventor: Tsuyoshi Watanabe, 198-2, Nozuta-cho, Machida-shi, Tokyo, Japan

[21] Appl. No.: 391,940

[22] Filed: Aug. 10, 1989

[51] Int. Cl.$^5$ .............................. A61B 5/02
[52] U.S. Cl. ................... 128/691; 351/206; 128/745
[58] Field of Search .............. 128/745, 691; 351/206-208

[56] References Cited

U.S. PATENT DOCUMENTS

| | | | |
|---|---|---|---|
| 4,166,695 | 9/1979 | Hill et al. | 128/745 X |
| 4,249,825 | 2/1981 | Shapiro | 128/745 X |
| 4,331,132 | 5/1982 | Mukasa | 128/745 X |
| 4,579,430 | 4/1986 | Bille | 128/691 X |
| 4,848,897 | 7/1989 | Aizu et al. | 128/691 X |

Primary Examiner—Lee S. Cohen
Assistant Examiner—J. P. Lacyk
Attorney, Agent, or Firm—Wegner, Cantor, Mueller & Player

[57] ABSTRACT

The instrumentation of sizes of a retinal vessel in the fundus is carried out by measuring continuously the sizes of the retinal vessel changing in accordance with heart beats at a site preset on the arteriole or the venule of the retinal vessel from images of the retinal vessel in the fundus continuously taken by a television camera or other photographic means; and comparing a periodical change of the sizes of the arteriole or venule of the retinal vessel. Static images are extracted at a given interval from fundus images photographed continuously by a television camera or recorded in a video tape recorder and converted into digital image which, in turn, is subjected to image processing. A length of the processed image data is measured at a given site of the image data fetched at a given timing from a storage, and a graph of rectangular coordinates is formed with a time coordinate versus a coordinate of measured values.

9 Claims, 11 Drawing Sheets

ACCELERATION PULSE WAVE

ACCELERATION PULSE WAVE

ACCELERATION PULSE WAVE

AGE 65 B.P 126/76

ACCELERATION PULSE WAVE

ACCELERATION PULSE WAVE

ACCELERATION PULSE WAVE

ACCELERATION PULSE WAVE

ACCELERATION PULSE WAVE

← GOOD  NO GOOD →

METHOD FOR THE INSTRUMENTATION OF SIZES OF RETINAL VESSELS IN THE FUNDUS AND APPARATUS THEREFOR

BACKGROUND OF THE INVENTION

1. Field of the Invention

The present invention relates to a method for the instrumentation of sizes of retinal vessels in the fundus and an apparatus therefor and, more particularly, to a method for the instrumentation of the blood circulation function, specifically, the instrumentation capable of detecting a state of the blood reflux from the state in which the retinal vessels in the fundus vary in correspondence with heart pulses, thus permitting an easy clinical evaluation of the microvasculature circulation.

2. Description of Related Art

The retinal vessels in the fundus are the ones that can be observed directly from the outside so that they are utilized for the internal diagnosis of disorders of circulatory organs, diabetes and so on as well as for the ophthalmologic diagnosis by an ophthalmoscopic or photographic observation.

In order to permit a good circulation, it is important to allow the venous vessels to contract to an appropriate extent and to thereby retain no excessive amount of blood therein. For normal people, as a ratio in size of the arteriola to the venule is approximately 2 to 3, a ratio in size of the arteriola to the venule in the fundus is seen significant for evaluation to judge whether the blood circulation is good and a photography of the fundus is used as a means of testing the blood circulation function. It is noted, however, that sizes of the retinal arteriola and venule vary with heart pulses so that it is difficult in many cases to determine what are sizes of the retinal arteriola and venule at the maximum diastole and thus the conventional technique suffers the disadvantage in terms of a diagnosis accuracy. Currently, this technique is mainly used for observation for a discrepancy of sizes of the arteriola which arises as a symptom develops, and the arteriolae and so on at the stage of a pachynsis of vessel walls or other sclerosis.

SUMMARY OF THE INVENTION

The present invention has the first object to provide a method for the instrumentation of sizes of retinal vessels in the fundus.

The present invention has the second object to provide an apparatus for the instrumentation of sizes of the retinal vessels in the fundus.

The instrumentation is carried out by continuously measuring a state of retinal arteriola and venule in the fundus which are periodically expanded and contracted in association with the heart pulses. This enables an abnormality of the blood circulation function to be discovered clinically at initial stages from the sizes of the arteriola and venule and a state of change between the diastole and systole.

The method for the instrumentation of sizes of retinal vessels in the fundus involves measuring continuously values from pictures of the retinal vessels in the fundus continuously photographed by a television camera or the like, a value in which sizes of the retinal arteriola and venule at their predetermined sites change in correspondence with the heart pulses, and comparing a periodical change of the vessel sizes of the retinal arteriola and venule.

BRIEF DESCRIPTION OF THE DRAWINGS

Other objects, features and advantages of the present invention will become apparent in the course of the description of the preferred embodiments which follows in the light of the accompanying drawings, in which:

FIGS. 4(a) through 11(a) are graphs each showing instrumentation results obtained by the instrumentation apparatus according to the present invention;

FIGS. 4(b) through 11(b) are graphs each showing an acceleration pulse waveform obtained from a person tested;

DETAILED DESCRIPTION OF THE PREFERRED EMBODIMENTS

The instrumentation apparatus to be used for the method according to the present invention comprises a sampling unit for sampling static images in a given interval from the fundus pictures taken by a television camera and recorded on a video tape or taken continuously by a television camera, an image processing unit for converting the static images into digital images and subjecting them to definition processing, mask processing, and filter processing, a storage unit for storing a processed image data, an instrumentation unit for fetching the stored image data at a predetermined timing and instrumenting a length of a predetermined segment on a monitoring screen, an arithmetic processing unit for receiving outputs one by one from the arithmetic processing unit and forming an orthogonal graph of times and instrumented values, a monitoring unit for displaying the graph, and a recording unit for recording the graph.

Figure 1:
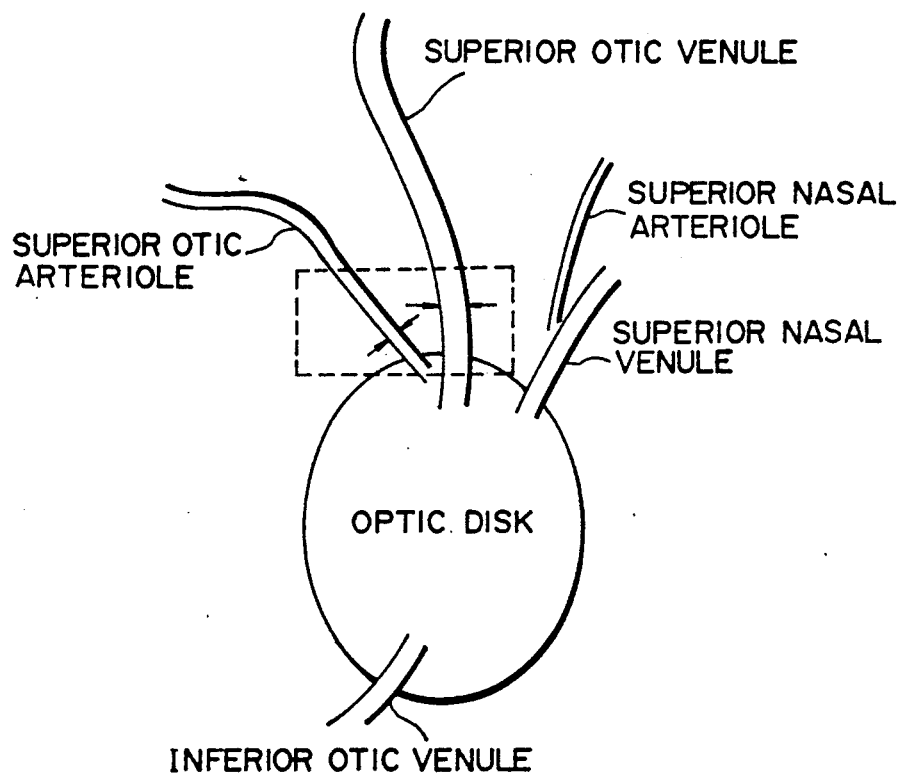
FIGS. 1 and 2 are each a schematic diagram showing a system of retinal vessels in the fundus.
Figure 2:
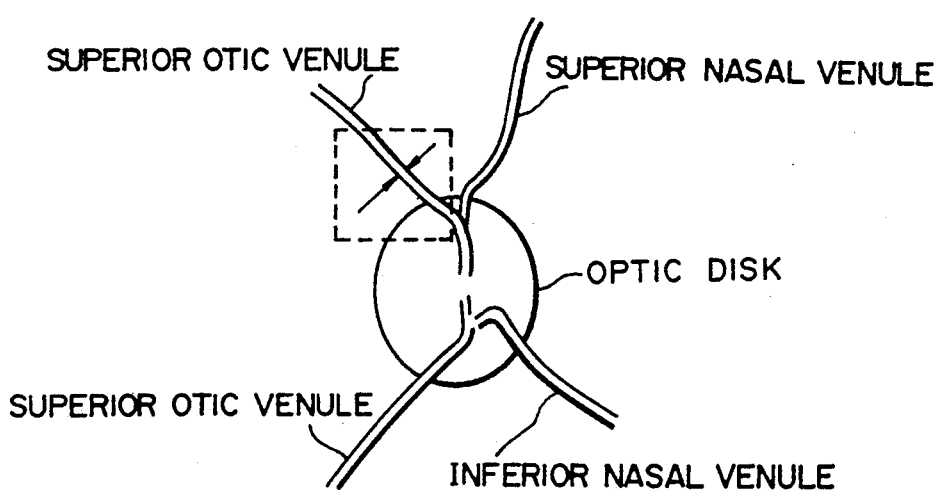

Referring to FIG. 1, the blood vessels leading from the optic disk comprise four pairs, such as superior otic arteriola and venula, inferior otic arteriola and venule, superior nasal arteriola and venule, and inferior nasal arteriola and venule. The image processing can be simplified by cancelling an image of the artery system by the mask processing as shown in FIG. 1 when the vein system is observed, on the one hand, and by cancelling an image of the vein system as shown in FIG. 2 when the artery system is observed. Furthermore, if one of the four pairs of the vessel groups is selected and the image processing is executed exclusively in a vicinity of the selected pair of the vessel group, a number of image data can be reduced and a processing time can be shortened. The instrumentation of the vessel sizes may be carried out using an image sensor on a monitoring screen or by vector operation of an instrument site of vessel image. In this case, an error may be produced in a magnification of an optical system and an enlargement or reduction of image. This error, however, may be corrected by calibration of the fundus photographs in comparison with an pre-photographed image of a metal wire having a diameter of about 0.2 mm, thus permitting an instrumentation of a correct vessel size.

The human body functions to retain some amount of the blood in the vein even at the rest when no large amount of the blood if required and the blood retained in the vein may serve as promoting the blood reflux in the vein for ensuring a quantity of the blood sufficient to fill the left atrium with by contraction when a supply of a large amount of the blood is required upon activation of the body and so on. If the contracting function of the vein is impaired or if the blood is retained in an excessive amount in the vein on account of the swelling of the vein or for other reasons, the quantity of the blood returning back to the right atrium becomes so small that the quantity thereof to be fed to the right ventricule becomes smaller, too, thus causing the difficulty of supplying a sufficient quantity of the blood to each of the intestines and organs. Thus observation for an extent to which the retinal venule in the fundus observable directly from the outside becomes swollen provides an extremely significant information on the evaluation of a state in the blood circulates in the vein.

Figure 4A:
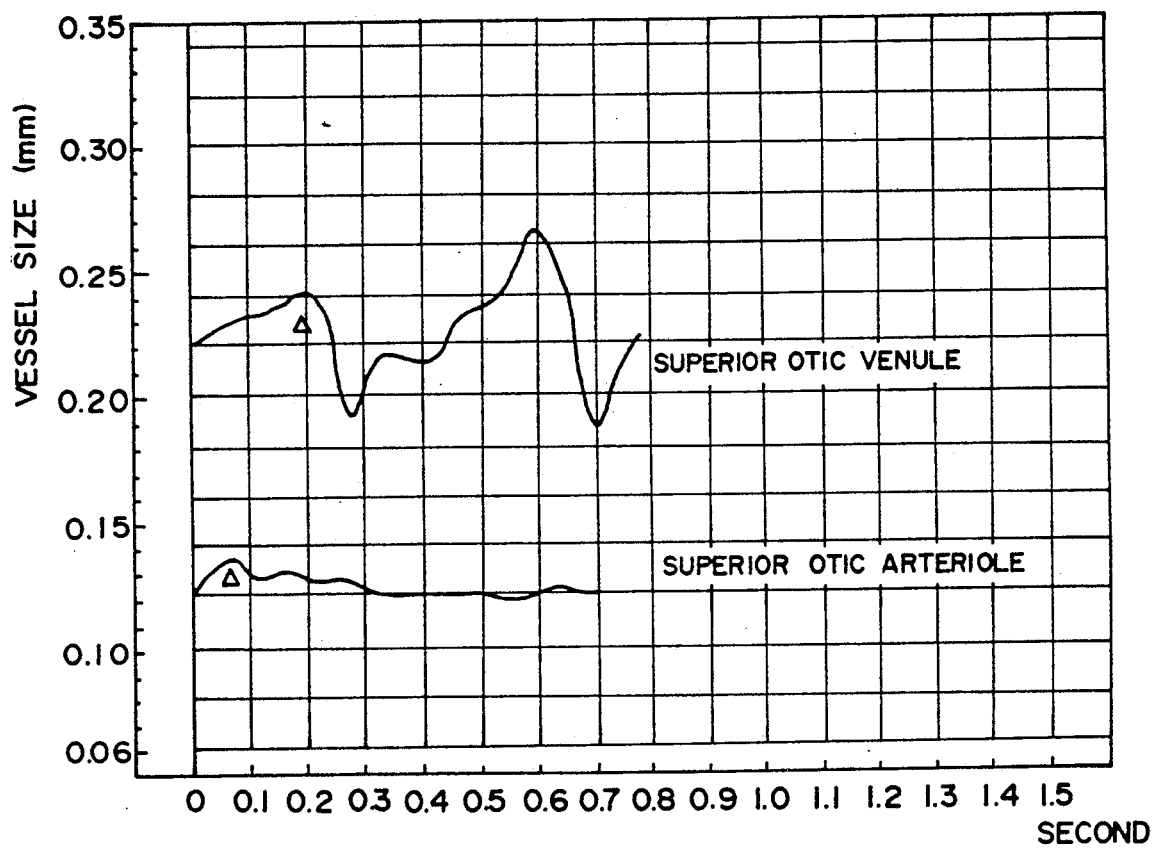
Figure 4B:
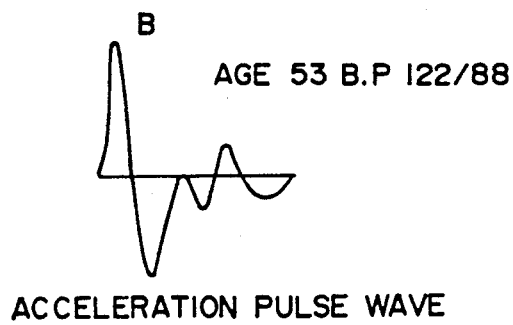

As shown in FIG. 4(a), the retinal venule in the fundus contracts or expands in association with the heart pulses so that it is extremely difficult to determine a stage of the retinal vessel which a particular fundus picture of the retinal venule represents from only a few fundus pictures. An observation for the state of the retinal vessel from only a small number of pictures may lead to a wrong evaluation for the state of the retinal vessels. In this sense, it is extremely difficult to provide a high accuracy of diagnosis. Thus an accurate and easy evaluation for a state of the venous reflux can be made from a graph represented by the relationship of a change of sizes of the retinal vessels in the fundus produced by the apparatus according to the present invention with an elapse of time.

The construction of a fundus image analysis apparatus according to the present invention will be described more in detail by way of example with reference to the accompanying drawings.

EXAMPLE 1

Figure 3:
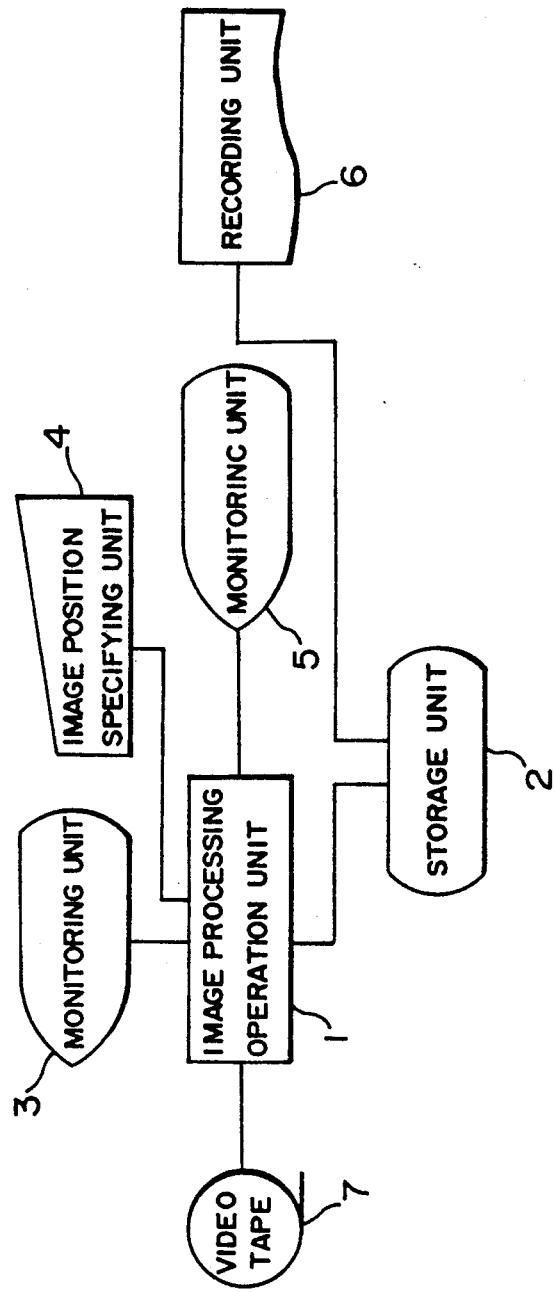
FIG. 3 is a block diagram showing one example of the instrumentation apparatus according to the present invention.

As shown in FIG. 3, fundus photos are taken with a television camera of twenty-five magnifications and recorded in a video type 7, and a region of the fundus photo is registered and input to an image processing unit 1 at a real time interval of 10 msec as a static image. Only a portion of the superior otic vein (an area indicated by the dotted line in FIG. 2) is cut by mask processing, and an unnecessary image is cancelled by filter processing after the definition processing. And the image of the superior otic vein is stored in a magnetic storage unit 2 as a binary image. A time image corresponding to one pulse of pulsation is likewise fetched and stored in a storage unit one by one after the image processing. The image stored in the storage unit is accessed one by one on a monitoring screen 3 and, as shown in FIG. 1, a minimum distance from the right-hand end to the left-hand end of an image (indicated by the arrow) set on the screen is computed by an image position register unit 4, and the resulting value is stored in the storage unit. A time image corresponding to one pulse time from sphygmic pulses of the ear collected at the time of photographing as a synchronization signal is processed one by one. After all processing has been finished, a graph with times as the abscissa and sizes of retinal vessels as the ordinate is displayed on a monitor 5. The graph is then recorded on a recording paper with a recording unit 6.

A graph of the arterial vessel can be obtained by subjecting to the same processing as above with the exception that a region is exchanged at the stage of the mask processing and an image of the venous image is cancelled.

FIGS. 4(a) to 11(a) each shows a time graph obtained as above and corresponding to one pulse time recorded on a recording apparatus 6. In FIGS. 4(a) to 11(a), the lower line represents a periodical variation in sizes of the arteriola and the upper line represents a periodical variation in sizes of the venule.

FIGS. 4(b) to 11(b) each shows an acceleration pulse waveform of a person tested, in which the numerals represent an age of the person tested as well as blood pressures at the systole and at the diastole of the person tested. Data shown in FIGS. 4(a) to 11(a) and data shown in FIGS. 4(b) to 11(b) are of the same person tested, respectively.

Figure 13:
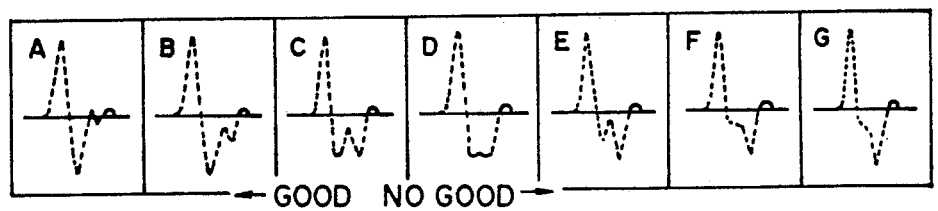
FIG. 13 is a view for explaining various patterns of an acceleration pulse waveform as an indicator of the blood circulation function.

FIG. 13 shows seven typical patterns A to G of an acceleration pulse waveform as an indicator of the blood circulation function, in which the patterns A to C reveal that the blood circulation function is normal, respectively, while the other patterns D to G reveal that the same is impaired, respectively. The acceleration pulse waveforms shown in FIGS. 4(b) to 6(b) correspond to the pattern B in FIG. 13, while the waveforms shown in FIGS. 7(b) and 8(b) correspond to the pattern C in FIG. 13. Further, the waveforms shown in FIGS. 9(b) and 11(b) correspond to the pattern D in FIG. 13, while the waveform shown in FIG. 10(b) correspond to the pattern E in FIG. 13.

FIG. 4(a) shows a graph of a person whose acceleration plethysmogram is normal, but the systolic blood pressure seems to be somewhat high (see FIG. 4(a)). According to FIG. 4(a) it is found that during one pulse of the heart, the venule is kept expanding even after it starts constricting and then it rapidly contracts, then it starts expanding and continues to expand up to a level higher than the previous expansion followed by contraction. A variation in the arteriola is monotonous rather than that in the venule. During one pulse, the arteriola once expands as well as then it contracts and converges to a constant size.

Figure 5A:
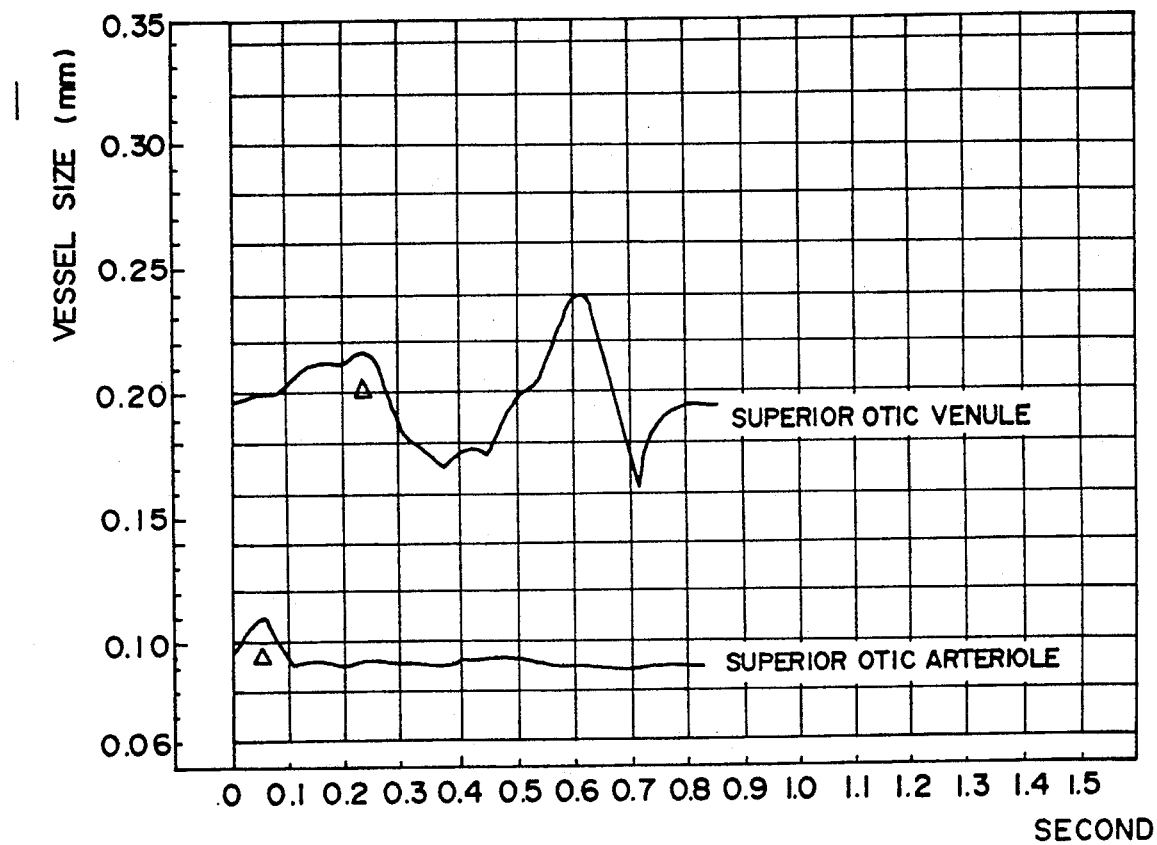
Figure 5B:
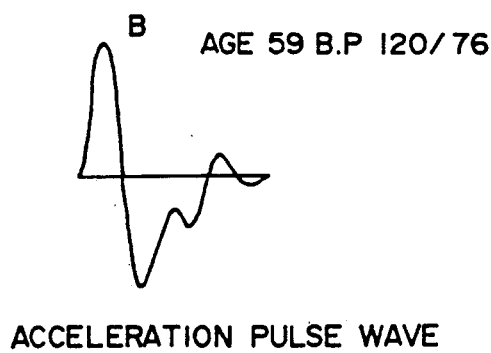
Figure 6A:
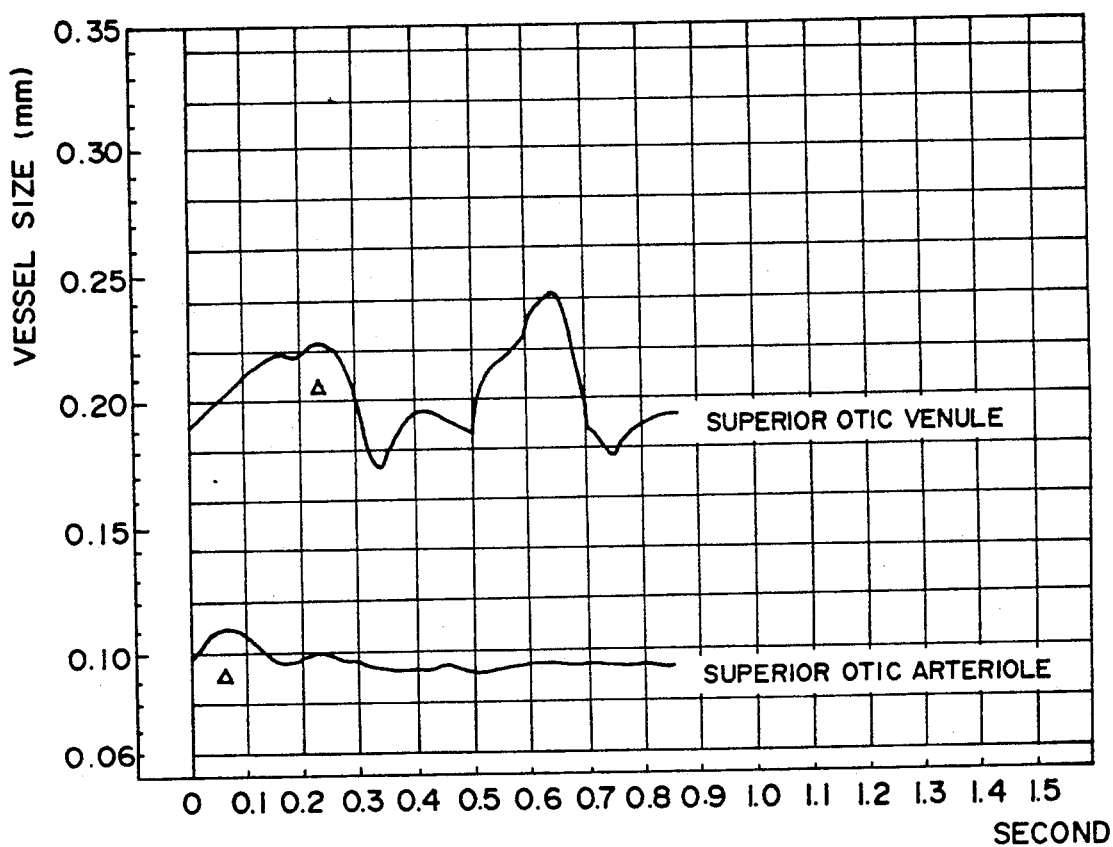
Figure 6B:
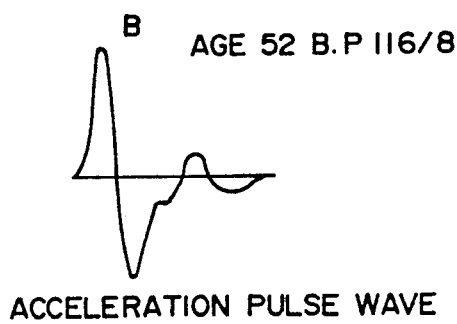
Figure 7A:
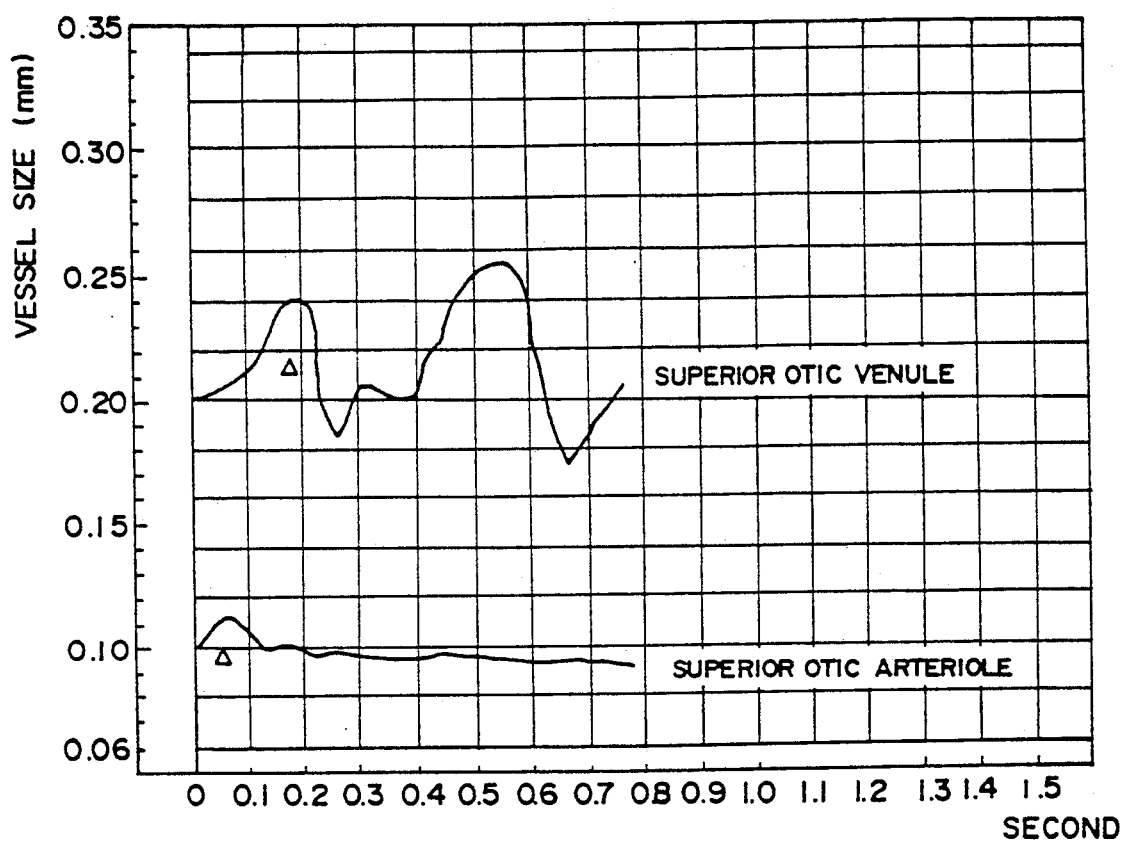
Figure 7B:
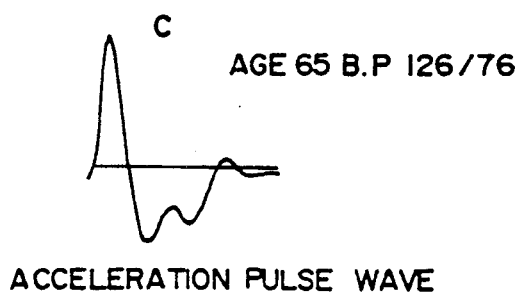

FIGS. 5(a), 6(a), and 7(a) show graphs of persons who have the normal blood pressures and the normal acceleration pulse waveform (see FIGS. 5(b), 6(b), and 7(b)). The graphs of the sizes of the venules reveal that they have in each case two peaks and valleys like FIG. 4(a) and that the size of the venule is somewhat smaller than that of FIG. 4(a). In each case, it has been found that the maximum size of the venule is around 0.25 mm.

Figure 8A:
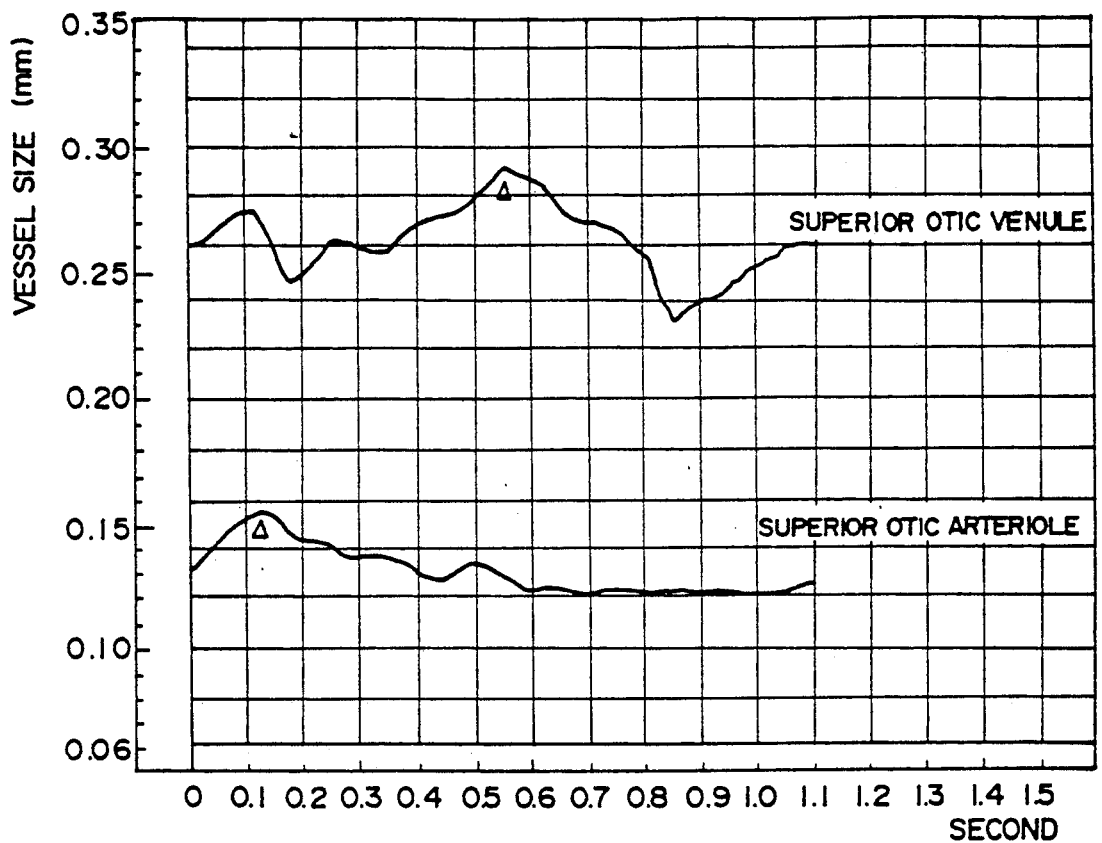
Figure 8B:
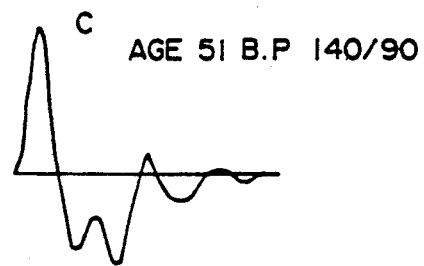
Figure 10A:
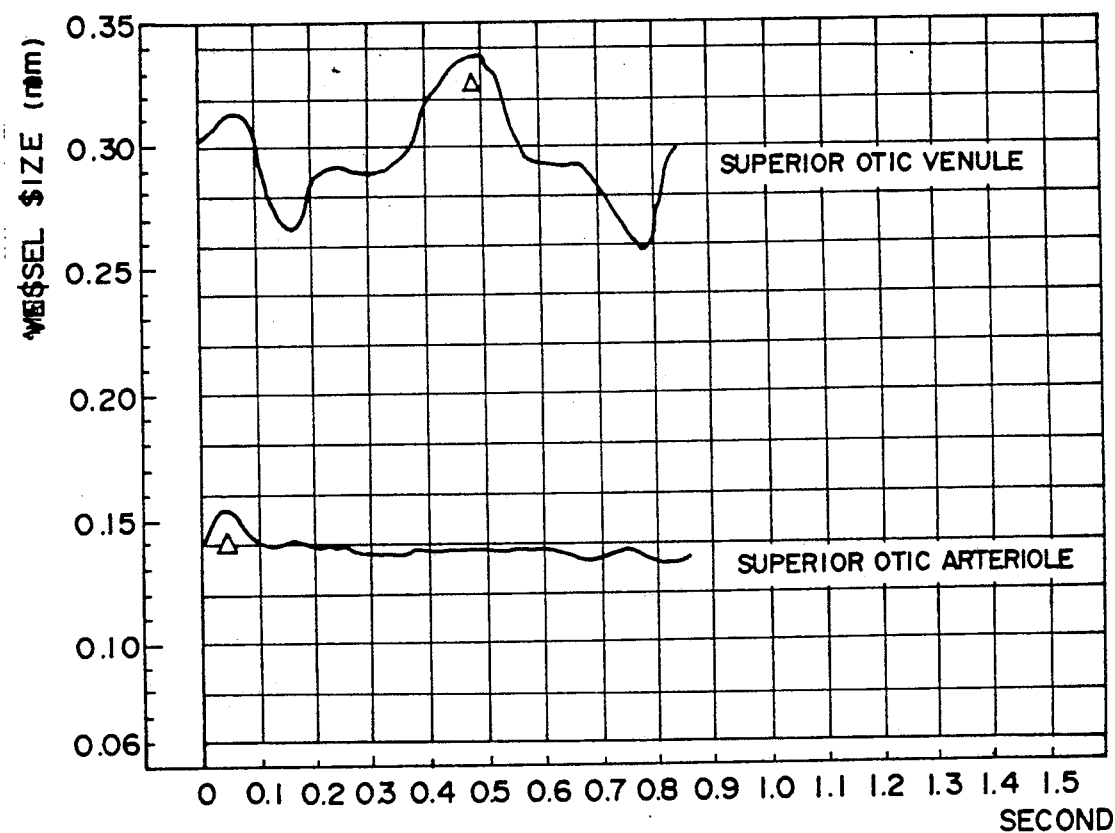
Figure 10B:
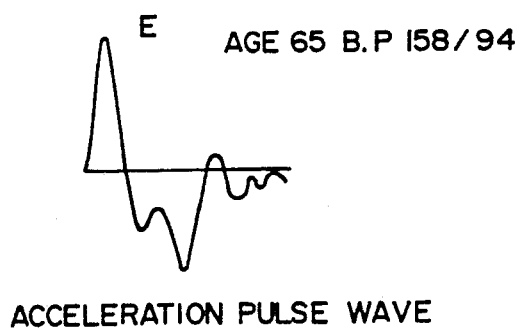

FIGS. 8(a) and 10(a) each shows a graph of a person suffering from borderline hypertension and impairing the blood circulation function when observed from the acceleration pulse waveform (see FIGS. 8(b) and 10(b)). The size of the venule in this case is transferred by approximately 20% upward of and in parallel to those shown in FIGS. 4(a), 5(a), 6(a) and 7(a).

Figure 9A:
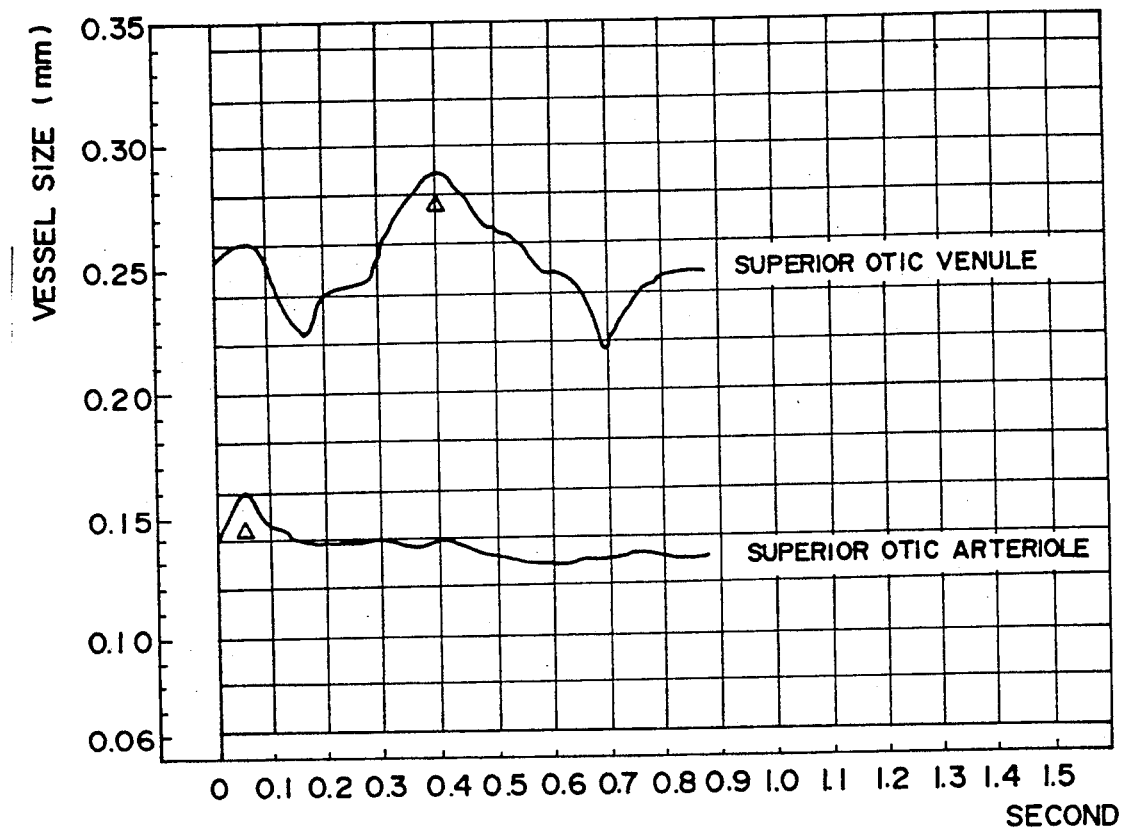
Figure 9B:
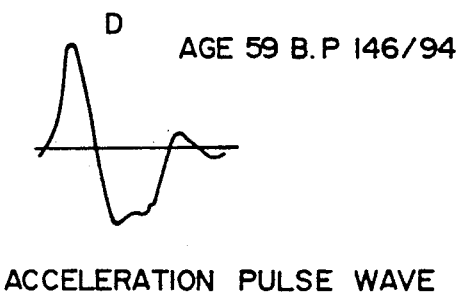
Figure 11A:
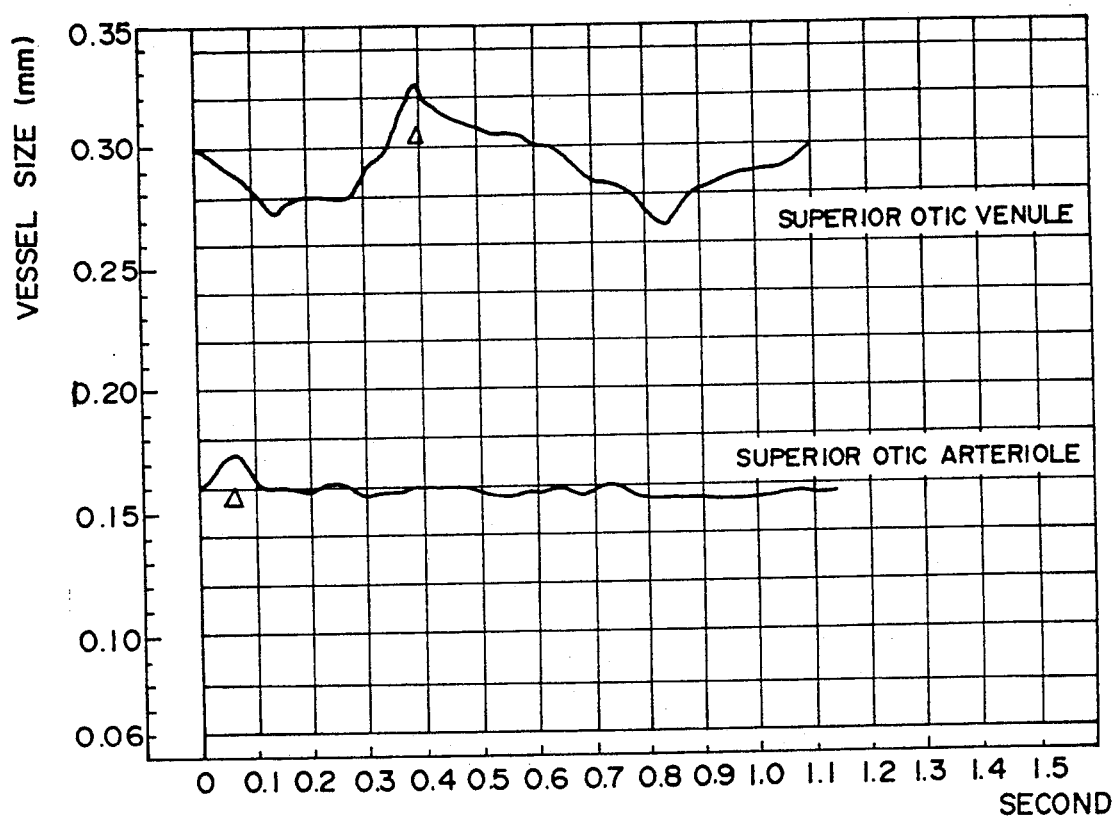
Figure 11B:
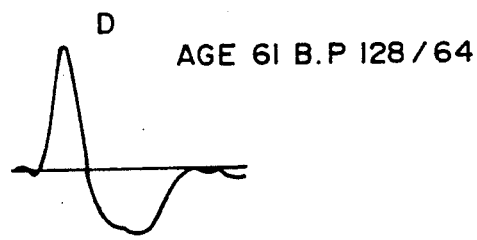

FIG. 9(a) shows a graph of a person who suffers from borderline hypertension and has the blood reflux impaired (see FIG. 9(b), FIG. 11(a) demonstrates a graph of a person whose blood pressures are normal yet whose acceleration pulse waveform shows the worsening of the reflux of the vein leading to the blood circulation function (see FIG. 11(b)).

In the above-mentioned four persons whose blood circulation functions are imparied, the peaks of the sizes of the venules (as shown by the symbol Δ in the graphs) are present around 0.3 mm and it is also observed from a deviation of their peaks from the corresponding peaks of the arteriolae (as shown by the symbol Δ in the graphs) that the expansion and contraction of the venule are slow. Furthermore, the fact that the size of the venule becomes larger indicates that an excessive quantity of the blood is retained in the venule.

As is apparent from the description as has been made hereinabove, a ratio of the arteriolar size to the venular size varies with time and a manner of variation differs from a state of the blood circulation function. For these reasons, it is impossible to make an accurate diagnosis from a smaller number of photographs showing static image, however, an observation for the graph obtained by the apparatus according to the present invention, which shows a periodical change of the sizes of the retinal venules in the fundus, permits a ready diagnosis of a change of the blood circulation function indicative of a sympton for cardiac disorders caused with adult diseases.

EXAMPLE 2

Figure 12:
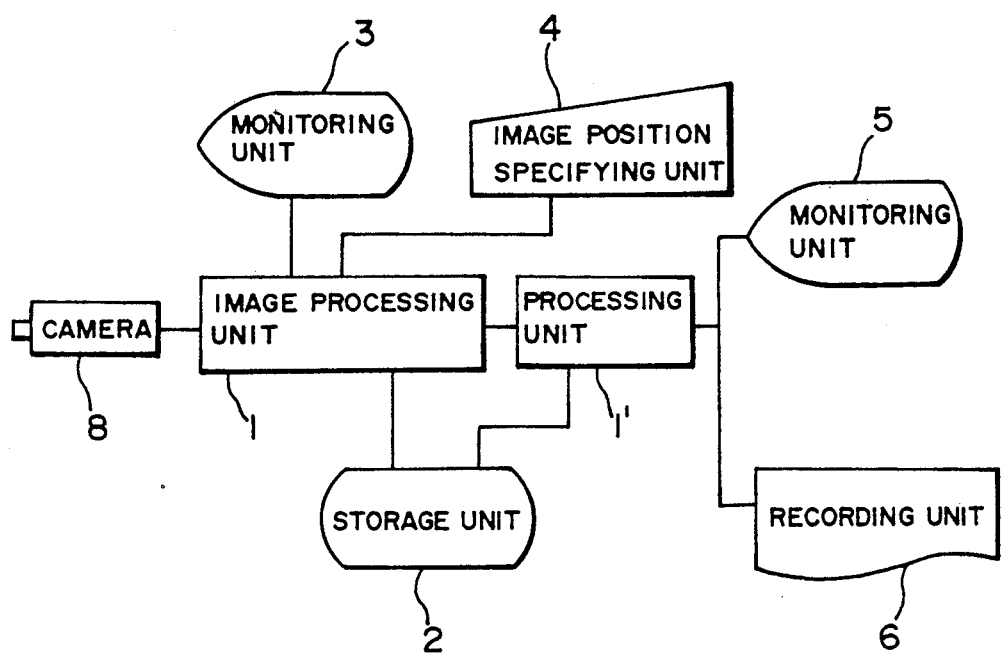
FIG. 12 is a block diagram showing another example of the instrumentation apparatus according to the present invention.

This Example is directed to an apparatus as shown in FIG. 12 in which an operation speed is enhanced by using an array processor. This apparatus thus permits a real-time processing of image recorded by the TV camera 8. In FIG. 12, the same elements are provided with the same reference numerals as in Example 1. It is to be noted, however, that data may be stored in an outside storage unit 2 and recorded by a recording unit 6 after a series of tests have been finished. For this purpose, an arithmetic processing unit 1' is provided for controlling the image processing unit 1, data storage unit 2, precording unit 6, and monitoring unit 5. This system is applicable to the continuous processing of a large number of test data from a group examination.

As have been described hereinabove, the present invention enables a continuous perception of a state of the retinal venule in the fundus which has been so far percepted in fragments, thus permitting a ready evaluation of a state of the venous reflux as an important information on the blood circulation function from a change in the sizes of the retinal venule in the fundus. The present invention further permits a discovery of abnormality in very initial stages in which the constancy of the living body begins getting lost and consequently an easy evaluation of diseases at their initial stages which have been conventionally diagnosed by investigating the fundus. Furthermore, the present invention enables a perception of a slight change so that can be practically applicable to evaluation of therapeutic results as an effective means.

It is to be understood that the present invention may be embodied in other specific forms without departing from the spirit and scope thereof. The present embodiments are therefore to be considered in all respects as illustrative and not restrictive, the scope of the invention being indicated by the appended claims, and all the changes, modifications and variations which come within the meaning and range of equivalency of the claims are therefore intended to be encompassed within the spirit and scope of the invention.

What is claimed is:

1. A method for the observation of the condition of blood circulation in the body, comprising the steps of:

taking a continuous video image of retinal vessels of the eye fundus;

sampling a series of static images of retinal vessels from the video image at predetermined time intervals during a time period which corresponds to at least one heart beat cycle;

measuring widths of respective images of retinal arterioles and venules at respective constant positions in each of the static images;

making a graph of periodical changes of the widths of the images of the retinal arterioles and venules as a function of the sampling timing of the static images; and displaying the graph on a monitor.

2. A method as claimed in claim 1, wherein the sampling of the static images comprises:

converting the sampled static images into digital images;

displaying the digital images on a monitor in the order of the sampled static images; and masking the digital images so as to selectively delete images of the retinal arterioles and venules from the digital image displayed on the monitor, said digital images from which the images of the retinal arterioles are delected being used for the measurement of the widths of the images of the retinal venules, while said digital images from which the images of the retinal venules are deleted are used for the measurement of the width of the images of the retinal arterioles.

3. An apparatus for the observation of the condition of blood circulation in the body, comprising:

means for taking a continuous video image of retinal vessels of the eye fundus;

means for sampling a series of static images of retinal vessels from the video image at predetermined time intervals during a time period which corresponds to at least one heart beat cycle;

means for measuring widths of respective images of retinal arterioles and venules at respective constant positions in each of the static images;

means for making a graph of periodical changes of the widths of the images of the retinal arterioles and venules as a function of the sampling timing of the static images; and means for displaying the graph on a monitor.

4. An apparatus as claimed in claim 3, wherein said video image taking means comprises a television camera and a video recorder for recording the continuous video image of the retinal vessels of the fundus on a video recording medium.

5. An apparatus as claimed in claim 3, wherein said sampling means comprises:

means for converting the sampled static images into digital images;

means for displaying the digital images on a monitor in the order of the sampled static images; and means for masking the digital images so as to selectively delete images of the retinal arterioles and venules from the digital image displayed on the monitor, said digital images from which the images of the retinal arterioles are deleted being used for the measurement of the widths of the images of the retinal venules, while said digital images from which the images of the retinal venules are deleted are used for the measurement of the widths of the images of the retinal arterioles.

6. An apparatus as claimed in claim 5, wherein said sampling means further comprises means for storing the digital images from which the images of the retinal arterioles and venules are selectively deleted on a recording medium.

7. An apparatus as claimed in claim 3, wherein said measuring means includes an image sensor for detecting the widths of the respective images of retinal arterioles and venules at the respective constant positions in each of the static images.

8. An apparatus as claimed in claim 3, wherein said measuring means includes means for performing vector processing of the respective images of retinal arterioles and venules at the respective constant positions in each of the static images in a transverse direction thereof.

9. An apparatus as claimed in claim 3, further comprising means for storing the graph on a recording medium.

* * * * *